United States Patent
Kobayashi

(10) Patent No.: US 8,794,761 B2
(45) Date of Patent: Aug. 5, 2014

(54) IMAGING APPARATUS AND METHOD FOR TAKING IMAGE OF EYEGROUND BY OPTICAL COHERENCE TOMOGRAPHY

(75) Inventor: Shuichi Kobayashi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 160 days.

(21) Appl. No.: 13/131,008

(22) PCT Filed: Dec. 24, 2009

(86) PCT No.: PCT/JP2009/007169
§ 371 (c)(1),
(2), (4) Date: May 24, 2011

(87) PCT Pub. No.: WO2010/073655
PCT Pub. Date: Jul. 1, 2010

(65) Prior Publication Data
US 2011/0228222 A1  Sep. 22, 2011

(30) Foreign Application Priority Data
Dec. 26, 2008  (JP) .................................. 2008-333869

(51) Int. Cl.
*A61B 3/14* (2006.01)
*A61B 3/10* (2006.01)

(52) U.S. Cl.
CPC ................. *A61B 3/14* (2013.01); *A61B 3/1015* (2013.01); *A61B 3/102* (2013.01)
USPC ............ 351/206; 351/205; 351/210; 351/221

(58) Field of Classification Search
CPC ...... A61B 3/14; A61B 3/1225; A61B 3/1015; A61B 3/102
USPC .......................... 351/205, 206, 210, 221, 246
See application file for complete search history.

(56) References Cited

U.S. PATENT DOCUMENTS

| | | | |
|---|---|---|---|
| 5,321,501 A | 6/1994 | Swanson | |
| 6,276,798 B1 * | 8/2001 | Gil et al. | 351/206 |
| 6,341,036 B1 | 1/2002 | Tearney et al. | |
| 7,952,723 B2 * | 5/2011 | Kobayashi | 356/497 |

(Continued)

FOREIGN PATENT DOCUMENTS

| | | |
|---|---|---|
| CN | 1947652 A | 4/2007 |
| EP | 1775545 A | 4/2007 |
| JP | H08-252256 | 10/1996 |
| JP | 2000-193889 | 7/2000 |

(Continued)

*Primary Examiner* — Huy K Mai
(74) *Attorney, Agent, or Firm* — Canon U.S.A., Inc., IP Division

(57) ABSTRACT

An optical unit concentrates light beams from measurement-light paths at first and second irradiation positions on an eyeground. Next, a control unit controls a scanning unit so that the light beams concentrated at the first and second irradiation positions are scanned in first and second scanning areas of the eyeground and so that the first and second scanning areas overlap to form an overlap area. A tomographic-information acquisition unit acquires first tomographic information and second tomographic information in the first and second scanning areas from interference light. Third tomographic information is acquired from the first tomographic information and the second tomographic information in the first and second scanning areas on the basis of the first tomographic information and the second tomographic information in the overlap area.

32 Claims, 12 Drawing Sheets

(56) References Cited

U.S. PATENT DOCUMENTS

| | | |
|---|---|---|
| 2005/0219544 A1 | 10/2005 | Chan |
| 2007/0076217 A1 | 4/2007 | Baker |
| 2007/0188707 A1 | 8/2007 | Nanjo |
| 2007/0291277 A1 | 12/2007 | Everett |
| 2008/0088852 A1 | 4/2008 | Rogers |
| 2008/0259275 A1 | 10/2008 | Aoki |
| 2008/0284981 A1 | 11/2008 | Fercher |
| 2009/0021746 A1 | 1/2009 | Toida |

FOREIGN PATENT DOCUMENTS

| | | |
|---|---|---|
| JP | 2007-151631 | 6/2007 |
| JP | 2008-508068 A | 3/2008 |
| WO | WO2006015717 | 2/2006 |
| WO | 2006/054975 | 5/2006 |
| WO | WO2006/054116 A2 | 5/2006 |
| WO | 2006/077107 | 7/2006 |
| WO | 2007/127291 | 11/2007 |

\* cited by examiner

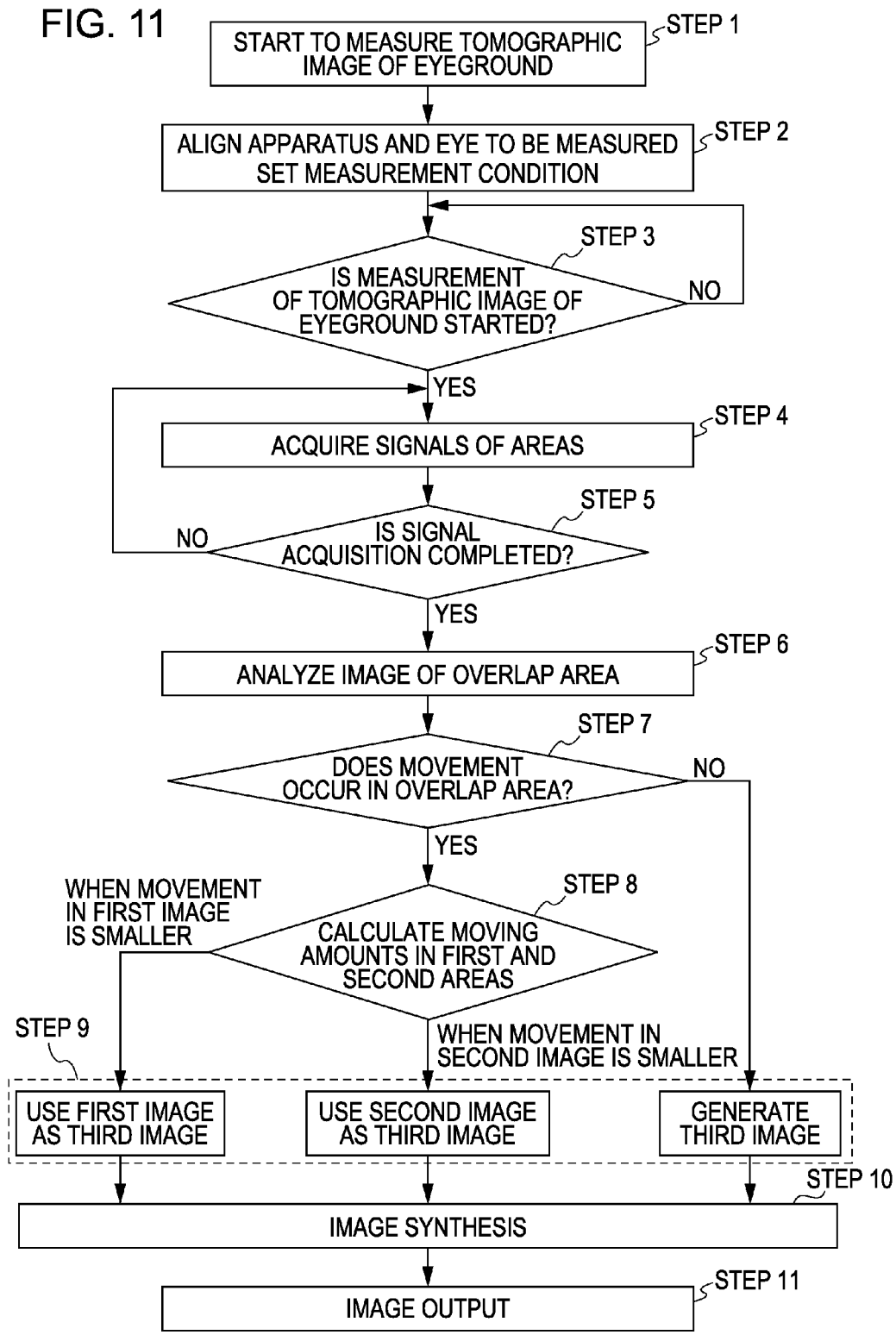

IMAGING APPARATUS AND METHOD FOR TAKING IMAGE OF EYEGROUND BY OPTICAL COHERENCE TOMOGRAPHY

TECHNICAL FIELD

The present invention relates to an imaging apparatus and method for taking an image of an eyeground by optical coherence tomography. More particularly, the present invention relates to a technique of acquiring accurate tomographic information about the eyeground at high speed by utilizing interference of low coherent light.

BACKGROUND ART

A technique of taking an image of an object to be examined by optical coherent tomography (hereinafter abbreviated as OCT) using low coherent light has been researched and developed as a high-resolution bioinstrumentation measurement technique. In particular, a disease of a retina can be accurately detected by the use of a tomographic image of the retina. For this reason, this technique is practically applied to a fundoscopy apparatus, and is further being researched and developed for higher performance.

OCT is roughly classified into two types. One type is time domain OCT (TD-OCT) for changing the position where a tomographic image is taken, by controlling the optical path length of reference light. The other type is Fourier domain OCT (FD-OCT) that can acquire data in the eye depth direction (optical-axis direction of the optical system) by one operation.

Fourier domain OCT is further classified into two types. One type is spectral domain OCT (SD-OCT) that splits interference light with a diffracted grating and detects the split light with a line sensor. The other type is swept-source OCT (SS-OCT) using a light source capable of wavelength sweeping. At present, spectral domain OCT is in the mainstream because it takes less time to acquire data in the eye depth direction than time domain OCT. In the case of a fundoscopy apparatus, the position of the eye is displaced because of the motion, blink, or involuntary eye movement of the subject during measurement, and this causes misalignment of images. For this reason, there is a demand to reduce the measurement time. Patent Literature 1 (PCT Japanese Translation Patent Publication No. 2008-508068) discloses OCT in which a plurality of light spots are applied onto the eye to acquire a three-dimensional structure of the eye.

CITATION LIST

Patent Literature

PTL 1: PCT Japanese Translation Patent Publication No. 2008-508068

SUMMARY OF INVENTION

Technical Problem

Patent Literature 1 (PCT Japanese Translation Patent Publication No. 2008-508068) mentions that a plurality of light beams are applied onto the eye so that a measurement area of each light beam becomes narrow to increase the measurement speed, but does not disclose acquisition of tomographic images of the eyeground with a plurality of light beams.

During acquisition of tomographic images of the eyeground, misalignment of tomographic images may be caused, for example, by involuntary eye movement. In this case, if tomographic images are acquired from a plurality of measurement areas with a plurality of light beams, the tomographic images may be misaligned. This makes it difficult to reconstruct a tomographic image of the entire measurement area on the basis of the tomographic images.

Solution to Problem

An optical coherent tomographic information acquisition apparatus according to an aspect of the present invention includes first and second interference units having reference-light paths and measurement-light paths; an optical unit configured to concentrate light beams from the measurement-light paths of the first and second interference units at first and second irradiation positions on an eyeground, the optical unit including a scanning unit configured to scan the concentrated light beams over the eyeground; a control unit configured to control the scanning unit so that the light beams concentrated at the first and second irradiation positions are scanned in first and second scanning areas of the eyeground and so that the first and second scanning areas overlap to form an overlap area; and a tomographic-information acquisition unit configured to acquire first tomographic information and second tomographic information in the first and second scanning areas from interference light beams in the first and second interference units. Third tomographic information is acquired from the first tomographic information and the second tomographic information in the first and second scanning areas on the basis of the first tomographic information and the second tomographic information in the overlap area.

An imaging apparatus according to another aspect of the present invention takes an image of an eyeground by optical coherence tomography. The imaging apparatus includes an optical unit configured to concentrate a plurality of measurement light beams incident on an anterior eye segment at a plurality of irradiation positions on the eyeground, and including a scanning unit configured to scan the concentrated measurement light beams over the eyeground; a tomographic-information acquisition unit configured to acquire tomographic information about the eyeground using the measurement light beams; and a control unit configured to control the scanning unit so that the measurement light beams concentrated at the irradiation positions are scanned in a plurality of scanning areas of the eyeground and so that adjacent scanning areas, of the plurality of scanning areas, overlap with each other.

An imaging method according to a further aspect of the present invention takes an image of an eyeground by optical coherence tomography. The imaging method includes a light concentration step of concentrating a plurality of measurement light beams incident on an anterior eye segment at a plurality of irradiation positions on the eyeground; a scanning step of scanning the concentrated measurement light beams in a plurality of scanning areas of the eyeground in a manner such that the adjacent scanning areas, of the plurality of scanning areas overlap with each other; and a tomographic-information acquisition step of acquiring tomographic information about the eyeground using the measurement light beams.

An imaging apparatus according to a still further embodiment of the present invention takes an image of an eyeground by optical coherence tomography. The imaging apparatus includes an optical unit configured to concentrate a plurality of measurement light beams incident on an anterior eye segment at a plurality of irradiation positions on the eyeground, and including a scanning unit configured to scan the concentrated measurement light beams over the eyeground; and a tomographic-information acquisition unit configured to acquire tomographic information about the eyeground using the measurement light beams. The optical unit concentrates the measurement light beams at the irradiation positions on the eyeground so that the measurement light beams intersect at the anterior eye segment.

Advantageous Effects of Invention

Since a plurality of light scanning areas of the eyeground overlap, even when misalignment between tomographic images is caused, for example, by involuntary eye movement, a tomographic image of the entire measurement area can be reconstructed from the tomographic images.

BRIEF DESCRIPTION OF DRAWINGS

FIG. 11 is a flowchart showing the third embodiment.

DESCRIPTION OF EMBODIMENTS

Figure 1A:
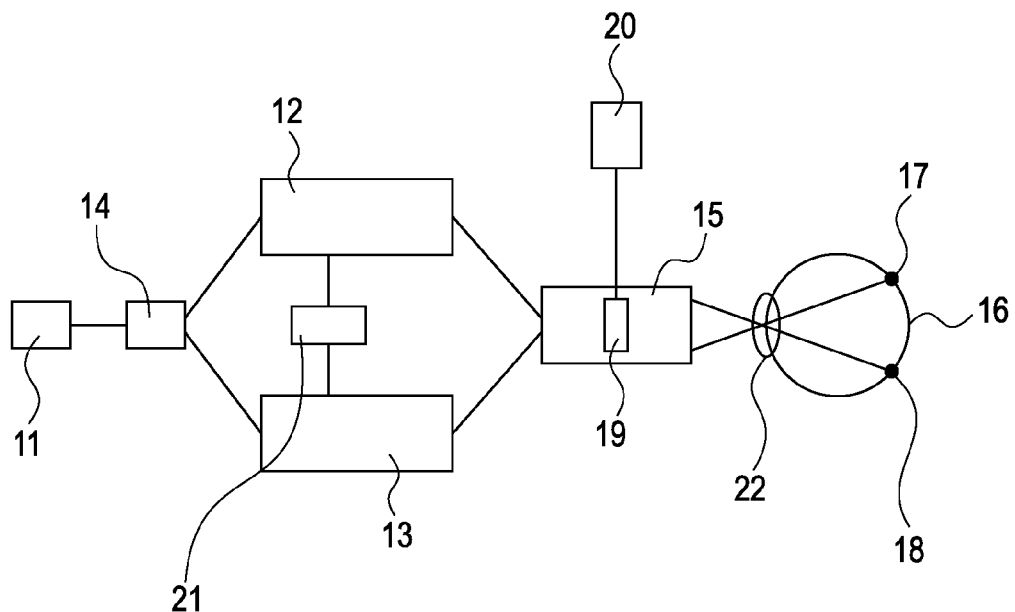
FIG. 1A is a schematic structural view of an optical coherent tomographic information acquisition apparatus according to an embodiment.

An optical coherent tomographic information acquisition device (also referred to as an imaging apparatus for taking an image of an eyeground by optical coherent tomography) according to an embodiment will be described with reference to FIG. 1A. The present invention is applicable to a Michelson interferometer or a Mach-Zehnder interferometer. Further, in the present invention, light may propagate in the space or through an optical fiber.

A light source 11 generates light. Preferably, the light source 11 is formed by a light source for generating low coherent light, for example, a super luminescent diode (SLD).

First and second interference units 12 and 13 each include a reference-light path and a measurement-light path. For example, the reference-light path and the measurement-light path correspond to a reference-light arm 107 and a measurement arm 111 in a first embodiment that will be described below.

A splitting unit (e.g., a beam splitter) 14 splits light from the light source 11 into a light beam to be guided to the first interference unit 12 and a light beam to be guided to the second interference unit 13. In the present invention, a plurality of light sources may be used without using the splitting unit. In other words, light beams from a plurality of light sources may be respectively guided to a plurality of interference units.

An optical unit 15 concentrates the light beams from the measurement-light paths of the first and second interference units 12 and 13 at first and second irradiation positions 17 and 18 on an eyeground 16. The optical unit 15 includes a scanning unit 19 for scanning the concentrated light beams over the eyeground 16.

Preferably, the optical unit 15 applies the light beams onto an anterior eye segment 22 of the human eye, and concentrates the light beams at the first and second irradiation positions 17 and 18 on the eyeground 16 via a pupil. Further preferably, the optical unit 15 includes a lens. In this case, when the light beams from the measurement-light paths of the first and second interference units 12 and 13 pass through the lens, dispersion occurs to each light beam. If the position where the light beam passes through the lens differs, the dispersion also sometimes differs. To compensate for the dispersion, first and second dispersion compensating units are preferably provided in the reference-light paths of the first and second interference units 12 and 13, respectively. For example, the dispersion compensating units correspond to an optical block 109 in the following first embodiment.

Preferably, the distance between spots of the light beams concentrated at the first and second irradiation positions 17 and 18 on the eyeground 16 is more than or equal to the sum of diameters (sizes or lengths) of the light spots (more than double the spot size when the spots have the same size). This can avoid interference between return light beams from the first and second irradiation positions 17 and 18. Hence, it is possible to acquire tomographic information with a high S/N ratio. This is because noise is caused in the acquired tomographic information if the return light beams from the first and second irradiation positions 17 and 18 interfere with each other.

An imaging apparatus that illuminates the eyeground with light from a light source serving as line illumination and detects an interference signal between reflected light from the eyeground and reference light by an area sensor is disclosed in Nakamura, "High Speed Three Dimensional Human Retinal Imaging by Line Field Spectral Domain Optical Coherence Tomography", Optics Express Vol. 15, No. 12 (2007). According to this paper, line illumination allows low coherent tomographic imaging to be performed without scanning, but crosstalk occurs because light signals enter the area sensor from close areas on the eyeground. Accordingly, crosstalk can be reduced by setting the distance between the spots to be more than or equal to the sum of the spot diameters, as described above. This allows acquisition of tomographic information with a high S/N ratio.

A control unit 20 controls the scanning unit 19 so that the light beams concentrated at the first and second irradiation positions 17 and 18 are scanned in first and second scanning areas of the eyeground 16 and so that the first and second scanning areas (or adjacent scanning areas of a plurality of scanning areas) overlap to form an overlap area. Preferably, the control unit 20 controls the scanning unit 19 so that the positions of the first and second scanning areas are correlated with each other. For example, in the following first embodiment, the first and second scanning areas correspond to scanning areas 145, and the overlap area corresponds to an overlap area 137.

A tomographic-information acquisition unit 21 acquires first tomographic information and second tomographic information from interference light beams in the first and second interference units 12 and 13, respectively. Preferably, the interference light beams in the first and second interference units 12 and 13 are obtained by interference between the return light from the eyeground 16 and the return light from the reference-light path.

Third tomographic information is acquired from the first tomographic information and the tomographic data. For example, the first tomographic information and the second tomographic information are synthesized. In this case, the first tomographic information and the second tomographic information can be easily synthesized by using the first tomographic information and the second tomographic information in the overlap area (for example, correcting misalignment between the first tomographic information and the second tomographic information). The third tomographic information is the tomographic information synthesized in the overlap area. Preferably, an image forming unit is provided to form a tomographic image from the synthesized information. The third tomographic information may be any of the first tomographic information, the second tomographic information, and the tomographic information synthesized in the overlap area. For example, the image forming unit corresponds to an image forming unit 161 in the following first embodiment.

Preferably, the first tomographic information and the second tomographic information overlap in a sub-scanning direction of the scanning (or in a direction substantially perpendicular to a scanning-area arrangement direction in which the first scanning area and the second scanning area are arranged). In this case, by using tomographic information in the overlap area, of a plurality of pieces of tomographic information acquired in a plurality of scanning areas (e.g., by calculating a correlation between tomographic images), tomographic images that are adjacent in the main scanning direction of the scanning (or the scanning-area arrangement direction) can be aligned. In the present invention, of course, image alignment can be performed in the sub-scanning direction by the above method, and the scanning-area arrangement direction may coincide with the main scanning direction.

A plurality of measurement light beams intersect in an anterior eye segment

Figure 1B:
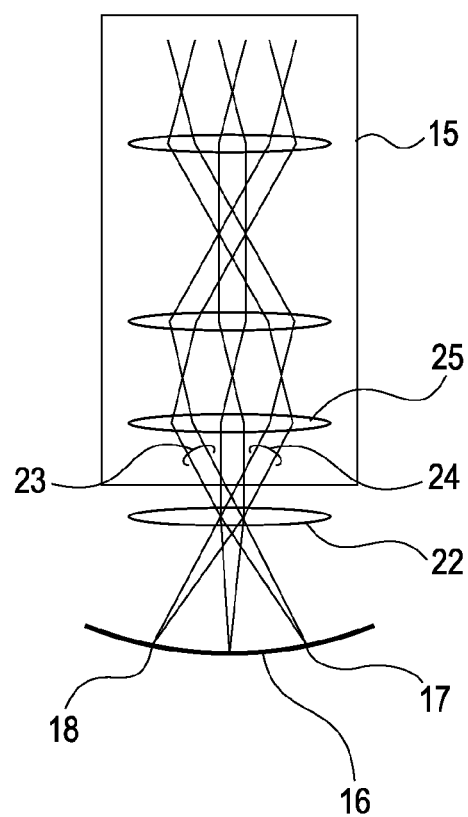
FIG. 1B is a schematic structural view of an optical coherent tomographic information acquisition apparatus according to another embodiment.

With reference to FIGS. 1A and 1B, a description will be given of an optical coherent tomographic information acquisition apparatus (also referred to as an imaging apparatus for taking an image of an eyeground by optical coherent tomography) according to another embodiment.

An optical unit 15 concentrates a plurality of measurement light beams incident on an anterior eye segment 22 (an optical system including a cornea and a crystalline lens, or including a cornea, a crystalline lens, and an intraocular lens) at a plurality of irradiation positions 17 and 18 on an eyeground 16. The optical unit 15 includes a scanning unit 19 for scanning the concentrated measurement light beams over the eyeground 16, and a tomographic-information acquisition unit 21 for acquiring tomographic information about the eyeground 16 with the measurement light beams. That is, light is applied onto the eyeground 16, and tomographic information about the eyeground 16 is measured using return light from the eyeground 16 and reference light. The optical unit 15 is configured in a manner such that the measurement light beams intersect in the anterior eye segment 22 and are concentrated at the respective irradiation positions. In other words, a plurality of incident light beams intersect in the anterior eye segment 22. It is preferable to adjust the relative position between the optical unit 15 (e.g., an eyepiece 25) and the anterior eye segment 22.

More specifically, the optical unit 15 applies first light 23 and second light 24 onto the eyeground 16 so that the first light 23 is concentrated at the first irradiation position 17 and the second light 24 is concentrated at the second irradiation position 18 different from the first irradiation position 17.

The first light 23 and the second light 24 intersect. The anterior eye segment 22 is located at a position where the first light 23 and the second light 24 intersect.

Japanese Patent Laid-Open No. 2006-195240 discloses an apparatus that applies a plurality of measurement light beams onto a sample, such as a living tissue or a living cell, with a microlens array disc (a structure in which a plurality of light-collecting lenses are arranged in an array) so as to form a plurality of convergent portions on the sample. In the apparatus disclosed in this publication, parallel light is applied onto the sample, and interference light between reflected light of the applied parallel light and reference light is detected to generate a tomographic image of the sample.

Japanese Patent Laid-Open No. 8-252256 discloses an optical coherent tomographic imaging apparatus including a plurality of light sources, an object-light imaging optical system and a reference-light imaging optical system common to the light sources, and optical sensors discretely located corresponding to the light sources. The apparatus disclosed in this publication applies light onto a planar imaging plane.

When applied onto the eyeground in an OCT apparatus for measuring tomographic information about the eyeground, a plurality of light beams need to first enter an anterior eye segment (a lens including a cornea and a crystalline lens or an intraocular lens). To diagnose a disease, it is required to apply a plurality of light beams onto an area wider than the anterior eye segment (a wider angle of view).

Accordingly, an OCT apparatus with a wider angle of view than in the related art can be achieved by concentrating a plurality of measurement light beams at a plurality of irradiation positions on the eyeground so that the measurement light beams intersect in the anterior eye segment, as described above. Here, it is preferable to correlate the positions of the areas where the first light 23 and the second light 24 are applied. This allows the incident position on the optical system to be grasped.

Preferably, a scanning mirror (or a scanning unit 19) is provided to scan the areas of the eyeground where the first light 23 and the second light 24 are applied. The scanning mirror is preferably located at a position conjugate to the anterior eye segment. This allows simultaneous control of a plurality of beams.

It is further preferable to provide a first reference mirror for reflecting reference light that interferes with the first light 23 and a second reference mirror for reflecting reference light that interferes with the second light 24. In addition, regarding the relative position between the first reference mirror and the second reference mirror in the optical axis direction of the optical unit 15, it is preferable to form a difference between the optical path length of the first light 23 and the optical path length of the second light 24. This can suppress image misalignment in the optical axis direction due to the difference in optical path length. The use of a single beam has the following problem. That is, when the angle of view (area where light is applied onto the eyeground) increases, when the beam passes through different optical paths in the optical system (e.g., a lens), the difference between the optical path lengths sometimes becomes larger than before. For this reason, control with only one reference mirror is difficult when the single beam is used.

First Embodiment

SD-OCT and Three Scanning Areas

Figure 2:
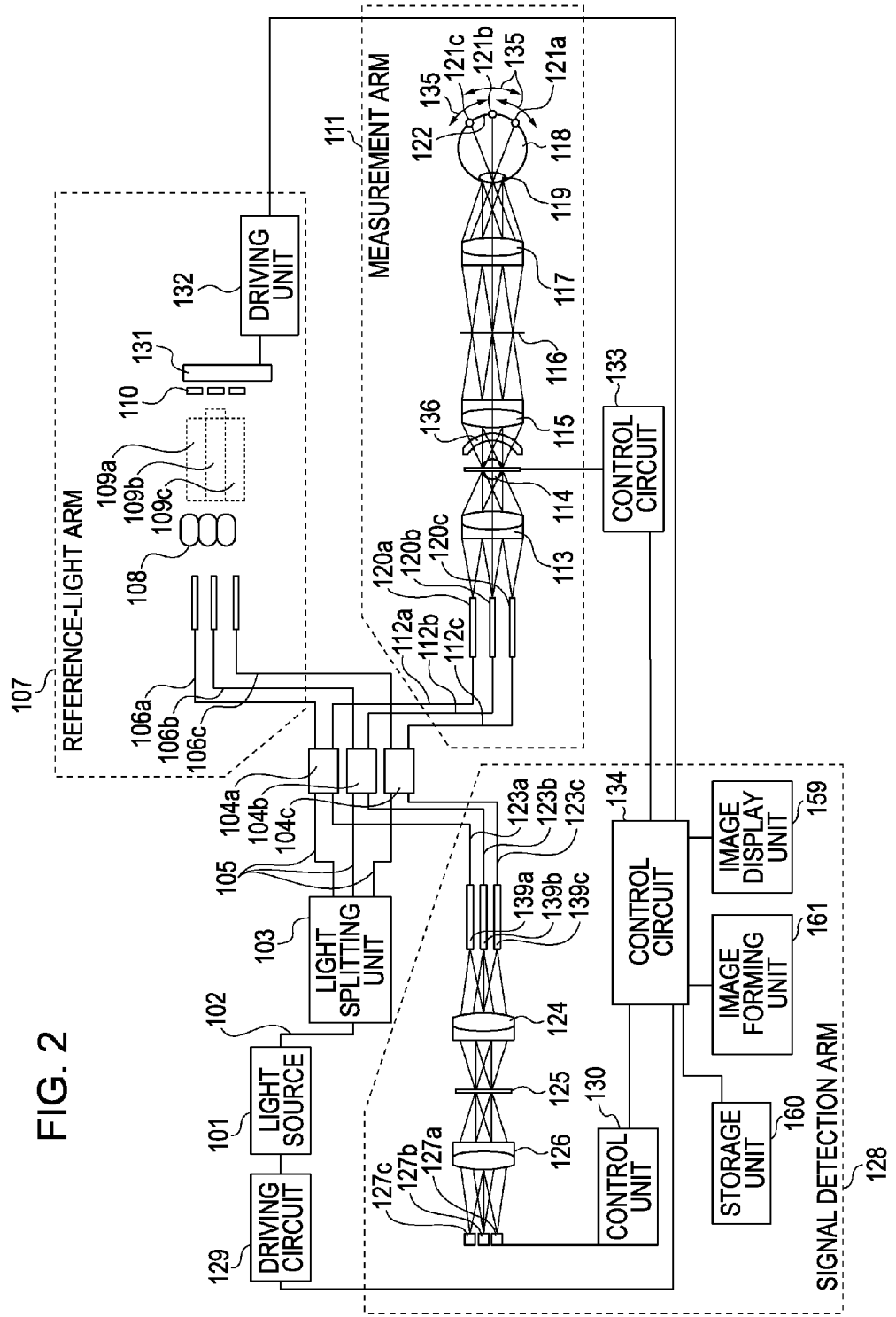
FIG. 2 is a schematic structural view showing a first embodiment.

A first embodiment will be described below. FIG. 2 schematically shows a configuration of the first embodiment.

A light source (optical coherent light source) 101 emits near-infrared low-coherent light. Light emitted from the light source 101 propagates through an optical fiber 102, and is split by a light splitting unit (beam splitter) 103 toward three optical fibers 105. The split light beams in the optical fibers 105 are split toward a reference-light arm 107 and a measurement arm 111 by optical couplers 104a, 104b, and 104c. The light source 101 is connected to a driving circuit 129 for driving the light source 101.

First, the reference-light arm 107 will be described below.

Near-infrared optical coherent light beams emitted from optical fibers 106a, 106b, and 106c (optical fibers for the reference-light arm 107) enter an optical block 109 (a glass block or a dispersion compensator) via collimating optical systems 108 (collimators). The light beams are then reflected by reflective mirrors 110, and enter the optical fibers 106a, 106b, and 106c again. The optical block 109 is composed of optical block elements 109a, 109b, and 109c corresponding to the optical paths of the light beams, and serves to compensate for dispersion of the optical system in the reference-light arm 107. The reflective mirrors 110 are connected to a control unit 131 for controlling the positions of the reflective mirrors 110 so that the optical path lengths can be controlled independently. Further, the reflective mirrors 110 are controlled by a driving unit 132 for driving the control unit 131.

Next, the measurement arm 111 will be described below.

The light beams split by the optical couplers 104a, 104b, and 104c respectively exit from fiber ends 120a, 120b, and 120c (exit ends) via optical fibers 112a, 112b, and 112c (optical fibers for the measurement arm 111). FIG. 2 shows a state in which a main scanning cross section of a scanning unit 114 (scanner) is taken along the optical axis. The light beams exiting from the fiber ends 120a, 120b, and 120c are made substantially parallel by an optical lens 113. The scanning unit 114 is located at a position such that the principal rays traveling from the light sources through the exit ends 120a, 120b, and 120c intersect at a deflection point in the scanning unit 114. The scanning unit 114 is formed by a galvanometer mirror having a rotatable mirror surface, and serves to deflect incident light. Further, the scanning unit 114 is connected to a control circuit 133 for controlling the scanning unit 114. Here, the scanning unit 114 is a two-dimensional scanning unit having two galvanometer mirrors, and can perform scanning in two directions, that is, the main scanning direction in the plane of the figure, and the sub-scanning direction perpendicular to the plane of the figure. The light beams scanned by the scanning unit 114 are caused by an imaging lens 115 to form conjugate images of the fiber ends 120 on an intermediate imaging plane 116. The light beams then pass through an objective lens (eyepiece) 117 and a pupil 119, and form irradiation spots 121a, 121b, and 121c corresponding to the fiber ends 120a, 120b, and 120c onto an eyeground (retina) 122 of an eye 118 to be examined. When subjected to in-plane deflection (in a direction 136) by the scanning unit 114, the irradiation spots 121a, 121b, and 121c move on the eyeground (retina) 122, as shown by arrows 135 (in a scanning-point moving direction). Areas where the irradiation spots move serve as scanning areas. Reflected light beams from the irradiation spot positions retrace the optical paths, enter the fiber ends, and then return to the optical couplers 104a, 104b, and 104c.

A signal detection arm 128 will be described below.

Interference light returning from the reference-light arm 107 and the measurement arm 111 is detected by the signal detection arm 128. Light beams propagating through optical fibers 123a, 123b, and 123c exit from fiber ends 139a, 139b, and 139c. The light beams exiting from the fiber ends 139a, 139b, and 139c are made parallel by a collimating lens 124, and enter a spectroscope (diffraction grating) 125. The spectroscope 125 has a periodical structure in the direction perpendicular to the plane of the figure, and splits light in that direction. The split light beams are focused onto line sensors 127a, 127b, and 127c by an imaging lens 126. The line sensors 127a, 127b, and 127c are connected to a control unit 130 for controlling the sensors so as to transmit predetermined acquired data to a storage unit 160. The data in the storage unit 160 is subjected to Fourier transformation by a control circuit 134 to form a tomographic image of the eyeground, and the tomographic image is output to an image display unit 159. The first embodiment provides a low coherent tomographic imaging apparatus for the eyeground using so-called Fourier domain OCT.

Since tomographic images are acquired from the three spots 121a, 121b, and 121c on the eyeground in the first embodiment, an image forming unit 161 is connected to correct images to be displayed on the image display unit 159.

Structures of the arms will be described in detail below.

Figure 3A:
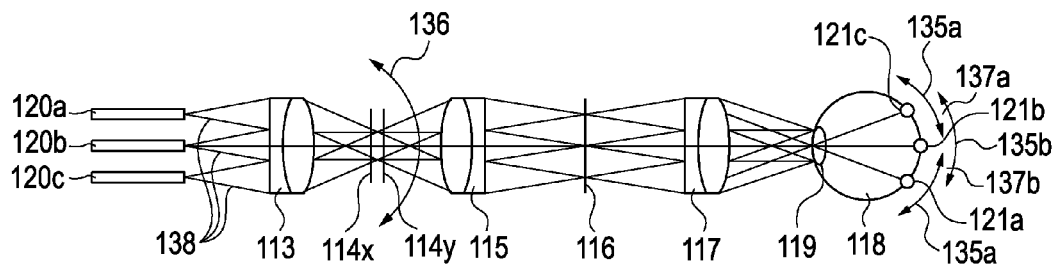
FIG. 3A is a schematic structural view of a measurement arm in the first embodiment.
Figure 3B:
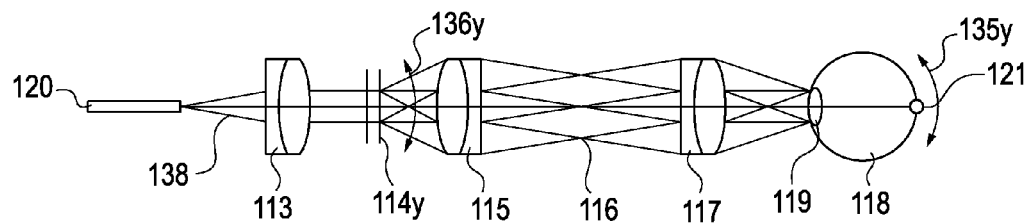
FIG. 3B is a schematic structural view of the measurement arm in the first embodiment.

FIGS. 3A and 3B are cross-sectional views of the measurement arm 111, respectively, taken in the main-scanning direction and the sub-scanning direction. Hereinafter, components denoted by like reference numerals have like functions, and descriptions thereof are omitted.

The scanning unit 114 includes a main scanning section 114x and a sub-scanning section 114y.

Light beams from the exit ends 120a, 120b, and 120c of the optical fibers are focused as the irradiation spots 121a, 121b, and 121c onto the eyeground (retina) 122 via the optical systems 113, 115, and 117. When scanned in the main scanning deflection direction shown by the arrow 136 in the scanning unit 114, the irradiation spots 121a, 121b, and 121c are scanned in scanning areas 135a, 135b, and 135c. In this case, overlap areas 137a and 137b are set between the scanning areas. Reference numeral 138 denotes radiation of the light beams.

Next, the structure of the cross section in the sub-scanning direction will be described. In a scanning direction 136y in the sub-scanning cross section, the irradiation spot 121 serving as a scanning point scans a scanning area 135y. By exerting control so as to synchronize scanning in the main scanning direction and scanning in the sub-scanning direction, raster scanning on the eyeground can be performed.

Figure 3C:
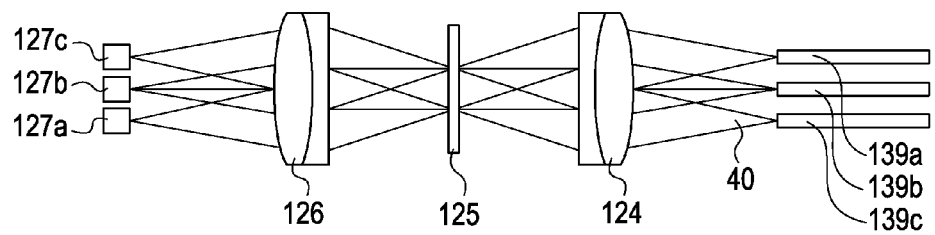
FIG. 3C is a schematic structural view of a signal detection arm in the first embodiment.
Figure 3D:
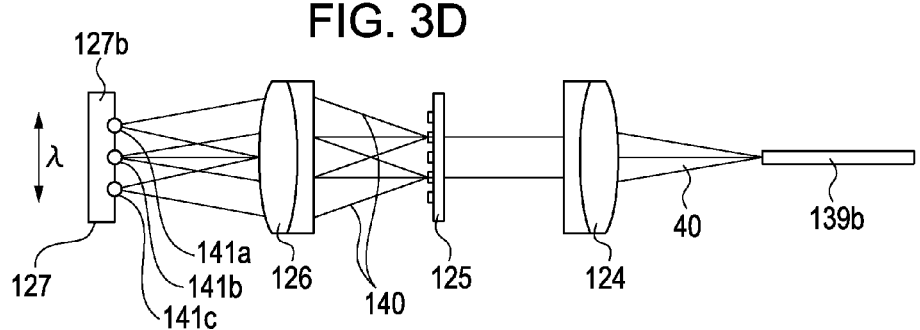
FIG. 3D is a schematic structural view of the signal detection arm in the first embodiment.

Next, the signal detection arm 128 will be described. FIGS. 3C and 3D are cross sectional views of an optical unit of the signal measurement arm 128, respectively, taken in an imaging direction and a spectral direction.

FIG. 3C shows a structure in which the light beams from the fiber ends 139a, 139b, and 139c are focused on the line sensors 127a, 127b, and 127c located at conjugate positions. As shown in FIG. 3C, the light beams from the fiber ends are focused onto the corresponding line sensors.

FIG. 3D shows the relationship between the fiber end 139b and the imaging point 127b. Light emitted from the fiber end is split at the spectroscope (diffraction grating) 125, and forms spectral spots 141a, 141b, and 141c on the area sensor 127 in accordance with the wavelengths. Since the spectrum of the light from the light source is a continuous spectrum, the light forms a line image on the area sensor. This spectrum is formed by light interference between the reference-light arm 107 and the measurement arm 111 in FIG. 2. A tomographic image is obtained by subjecting the intensity distribution on the line sensor to Fourier transformation. The pitch and shape of the spectroscope 125 are set, for example, in accordance with the spectrum of the light source 101.

Figure 4A:
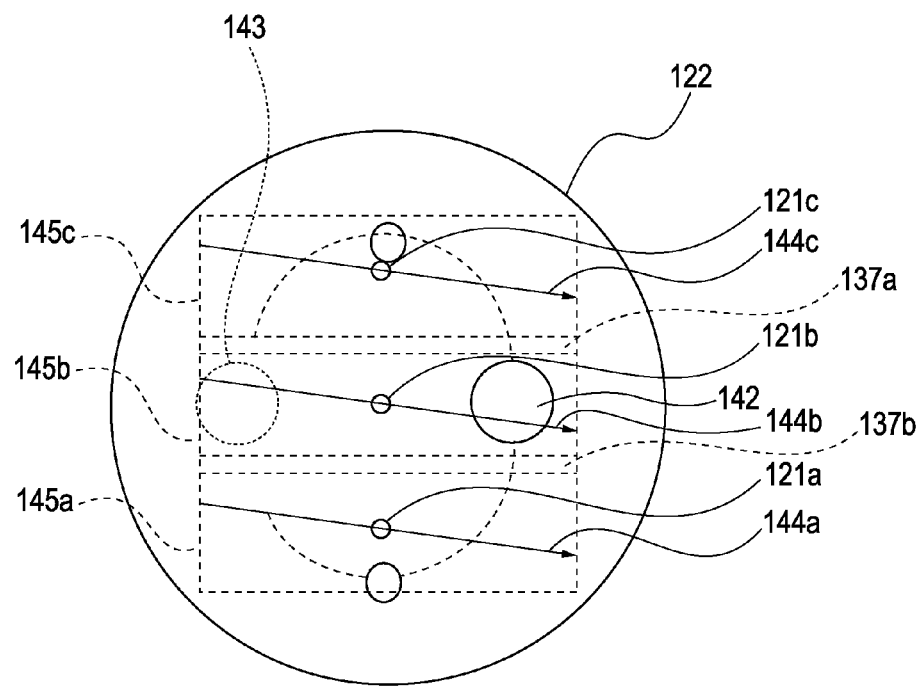
FIG. 4A is a structural view showing scanning areas in the first embodiment.
Figure 4B:
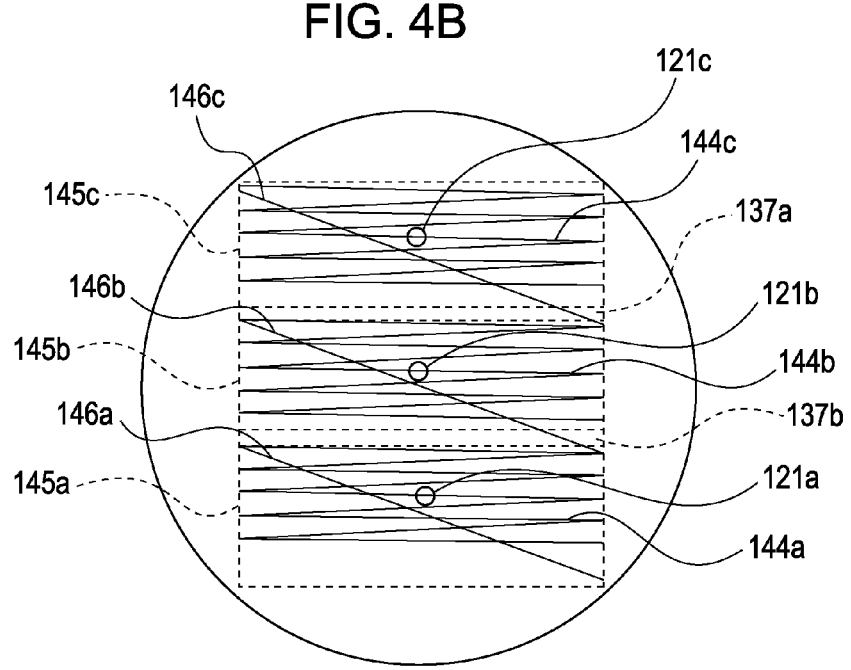
FIG. 4B is a structural view showing the scanning areas in the first embodiment.

FIGS. 4A and 4B show the scanning areas on the eyeground (retina) 122. For explanation, an optic disk 142 and a macula 143 are shown along with the eyeground (retina) 122. A description will now be given how to acquire a tomographic image of the retina near the optic disk 142 or the macula 143. Irradiation spots 121a, 121b, and 121c are formed at positions substantially equally spaced on the retina. Main scanning lines 144a, 144b, and 144c are provided corresponding to the irradiation spots 121, 121b, and 121c, respectively. In FIGS. 4A and 4B, scanning areas 145a, 145b, and 145c are scanned by a scanning unit (not shown). Overlap areas 137a and 137b are set between the scanning areas. The scanning areas are subjected to raster scanning for finer scanning, as shown in FIG. 4B. Scanning lines 146a, 146b, and 146c are retrace lines, and extend toward predetermined scanning points.

Figure 5A:
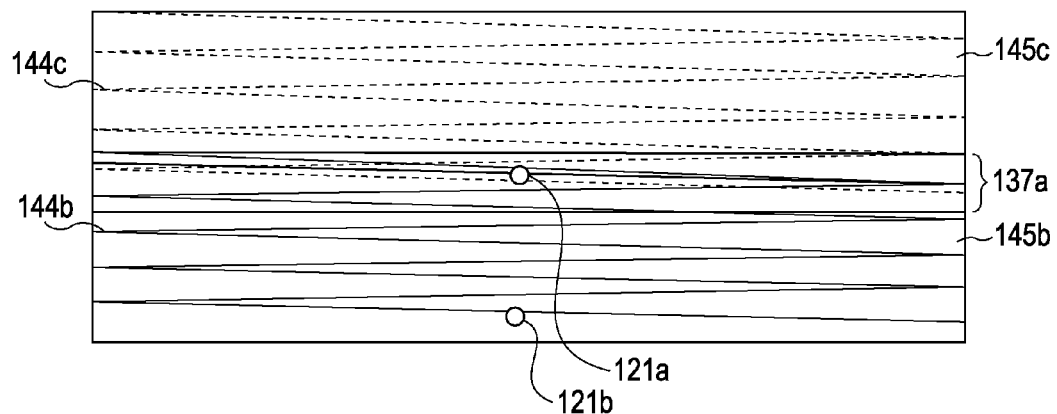
FIG. 5A is an explanatory view showing data formation in an overlap area.

FIG. 5A is an enlarged view of the overlap area 137a and its surroundings. The scanning areas 145c and 145b overlap with each other in the overlap area 137a set between the scanning areas 145c and 145b. The irradiation spots 121a and 121b perform raster scanning on the scanning lines 144c and 144b, respectively.

Figure 5B:
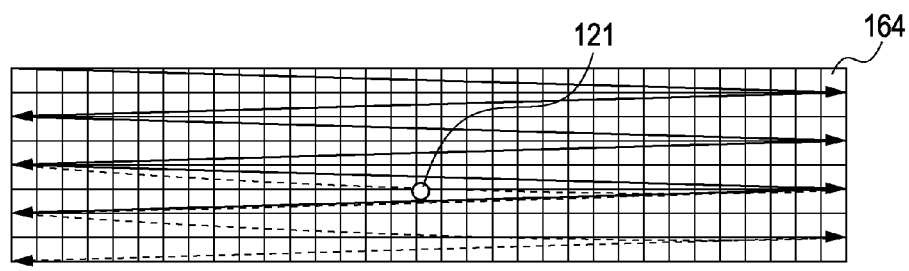
FIG. 5B is an explanatory view showing the data formation in the overlap area.
Figure 5C:
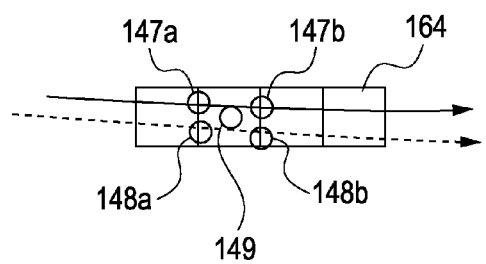
FIG. 5C is an explanatory view showing the data formation in the overlap area.

To acquire volume data by low coherent tomography of the eyeground, it is necessary to generate data on each point in a voxel 164, as shown in FIG. 5B. Outside the overlap areas, a voxel at a certain point can be assigned data at a near position. In contrast, in the overlap areas, there are data at a plurality of irradiation spots. Further, the scanning lines of the irradiation spots in the scanning areas do not coincide in the overlap areas. Generation of data on a voxel in this case will be described with reference to FIG. 5C. To generate data on a predetermined position 149 in the voxel 164, data on data acquisition positions 147a and 147b on a certain scanning line are taken out of the storage unit. Further, four data on data acquisition positions 148a and 148b on the scanning line of the irradiation spot different from the positions 147a and 147b are taken out of the storage unit. Then, data is generated by performing interpolation using the data positions and the data acquisition positions. In the overlap area 137, the scanning areas can be smoothly connected by interpolation using the data from the different scanning areas.

Figure 6:
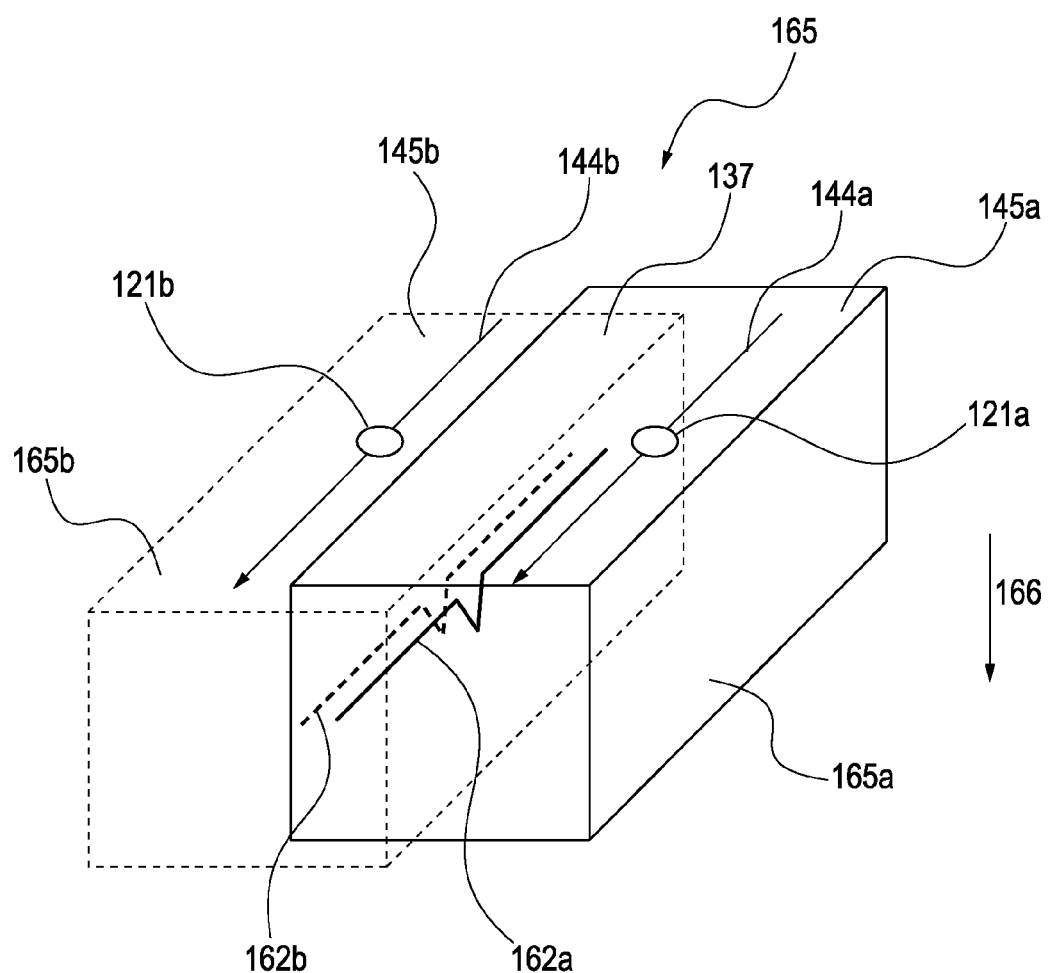
FIG. 6 is an explanatory view showing formation of volume data in the overlap area.

FIG. 6 shows generation of volume data 165 (165a, 165b). To acquire volume data 165a and 165b in the scanning areas 145a and 145b, it is necessary to perform data alignment in a tomographic direction 166 of the eyeground. For example, regarding the position in the tomographic direction, it is conceivable to adjust the position of the reflective minor 110 shown in FIG. 2 in each scanning area. Alternatively, it is conceivable to align images by extracting characteristic points from volume data on the scanning areas.

Reference numerals 162a and 162b denote tomographic images.

As described above, by simultaneously scanning a predetermined area by a plurality of spots, the data acquisition speed can be increased corresponding to the number of spots. In the first embodiment, the light source 101 can be formed by a super luminescence diode for emitting near-infrared light. Further, while light from one light source is split by the light splitting unit in the first embodiment, the present invention is not limited thereto, and a plurality of spots may be emitted from different light sources.

Figure 7A:
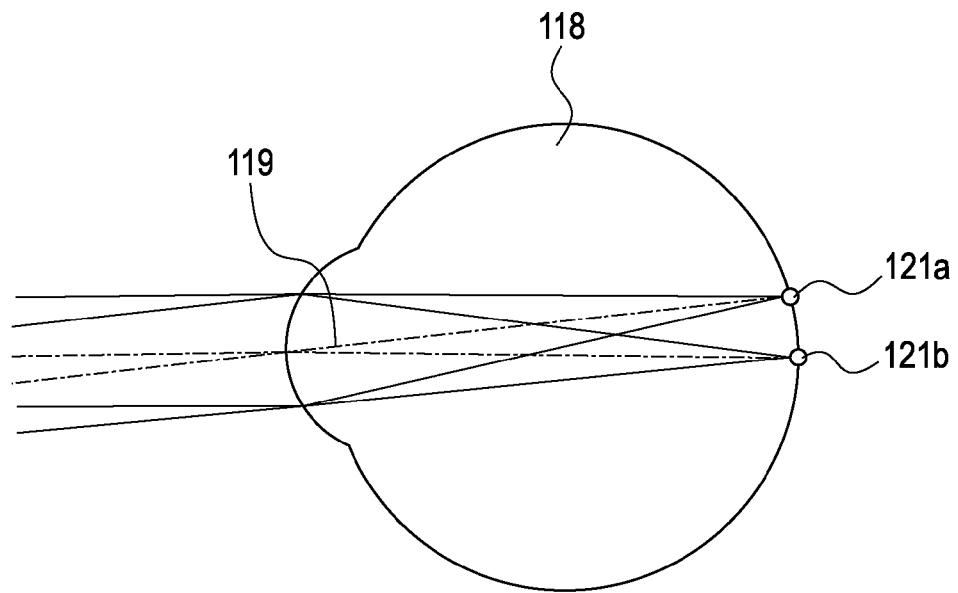
FIG. 7A is an explanatory view showing crosstalk at irradiation spots.
Figure 7B:
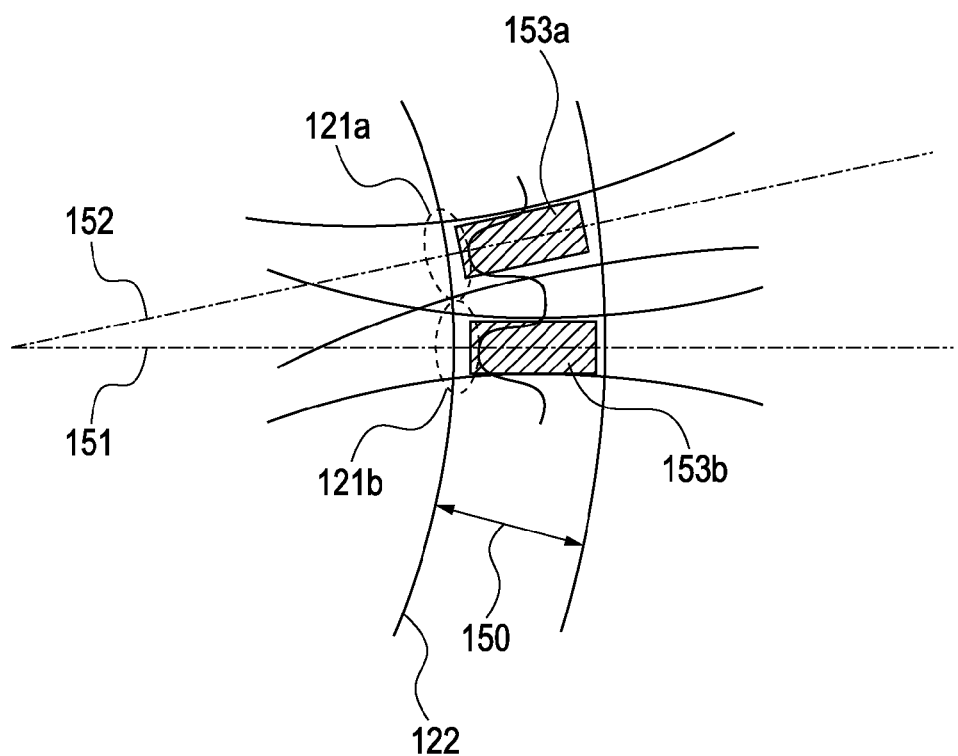
FIG. 7B is an explanatory view showing the crosstalk at the irradiation spots.

FIGS. 7A and 7B illustrate setting of the distance between the irradiation spots. FIG. 7A shows a state in which light is applied onto irradiation spots 121a and 121b of the eye 118 through the pupil 119. Reflected light beams from the spot positions enter the corresponding optical fibers (not shown) to form signal light. Since light scatters on the eyeground, if two irradiation spots are close to each other, their components produce noise. FIG. 7B illustrates setting of the distance in detail. The irradiation spots 121a and 121b on the eyeground 122 include focal-depth areas (coherent areas) 153a and 153b within a tomographic-image acquisition area 150 in the retina. For example, scattering in these areas causes crosstalk and noise. Assuming that the spot size on the eyeground is designated as "spot" in consideration of spreading of the spot on the surface of the retina, noise due to crosstalk can be reduced by setting the distance Wd between the irradiation spots as follows:

$$Wd > 2 * \text{spot} \tag{1}$$

While a plurality of irradiation spots are formed in the sub-scanning direction in the first embodiment, when it is assumed that the angle of view of the image acquisition area in the sub-scanning direction is designated as wh and the number of spots is designated as N, an angle ws between the spots is set as follows:

$$ws = wh/N \tag{2}$$

Assuming that the number of acquired data in the direction wh is Nd, a spot distance wsd is given as follows:

$$wsd = wh/Nd \tag{3}$$

When Nd>N, a noise reducing effect is achieved.

Reference numerals 151 and 152 denote light beams (convergent beams) that converge at the irradiation spots 121a and 121b, respectively.

While three line sensors are adopted in the first embodiment, as shown in FIG. 3C, similar advantages can also be obtained when three line sensors are combined in one or when images are formed on the area sensor.

Second Embodiment

Five Scanning Areas

A second embodiment will be described below. In the first embodiment, the eyeground is divided into three scanning areas, and the main scanning direction is set to be the right-left direction of the plane of the figure, as shown in FIGS. 4A and 4B. In contrast, in the second embodiment, the main scanning direction is set to be the up-down direction of the plane of the figure, and the eyeground is divided into five scanning areas. The configuration of the optical system can be similar to that shown in FIG. 2.

Figure 8A:
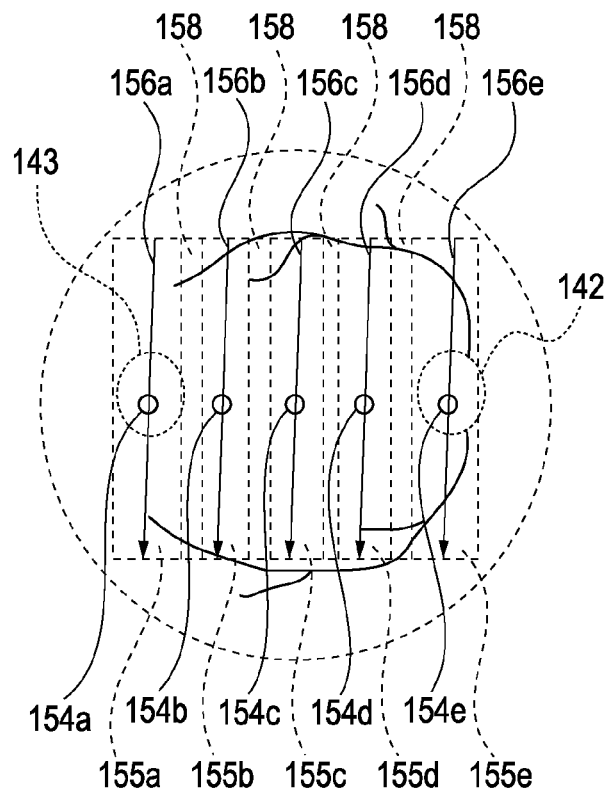
FIG. 8A is a schematic structural view showing a second embodiment.
Figure 8B:
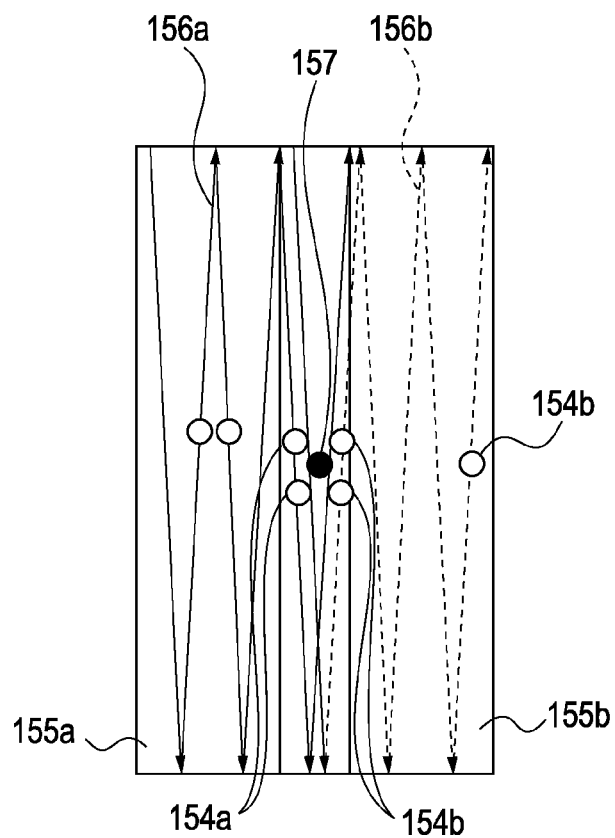
FIG. 8B is a schematic structural view showing the second embodiment.

FIGS. 8A and 8B explain area division on the eyeground in the second embodiment.

The eyeground is illuminated with five irradiation spots 154a, 154b, 154c, 154d, and 154e, and low coherent tomographic imaging is performed in areas of these irradiation spots. A reference-light arm and a signal detection arm (not shown) are provided for the irradiation spots. Reference numerals 156a to 156e denote scanning lines in the main scanning direction. Each irradiation spot is scanned over the eyeground by a scanning unit (not shown). In synchronization with scanning, low coherent tomographic data on the eyeground is acquired, and signals corresponding to the data are recorded by a recording unit (not shown).

In addition, overlap areas 158 are provided between the scanning areas. Similarly to the case shown in FIG. 5, data on the overlap areas are calculated by an image forming unit on the basis of data on the scanning areas recorded by the recording unit. For example, data on a specific position 157 is generated on the basis of data on positions 154a and 154b around the position 157.

Figure 9A:
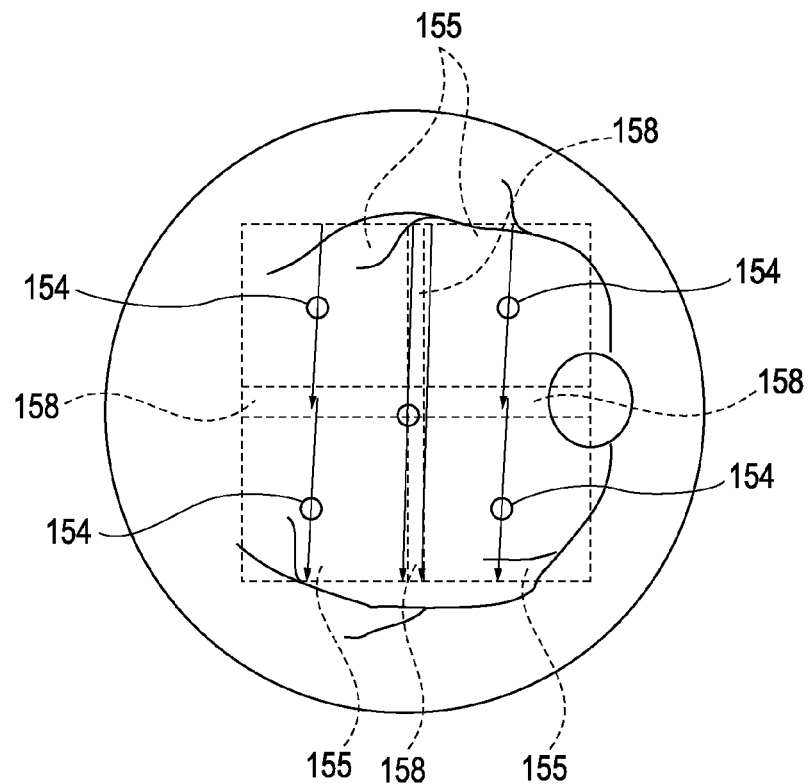
FIG. 9A is an explanatory view showing a modification of the second embodiment.

A modification of the second embodiment will now be described with reference to FIG. 9A. FIG. 9A shows a case in which the scanning area is divided into four scanning areas 155. In each scanning area 155, an irradiation spot 154 is scanned in the main scanning direction shown by the arrow and sub-scanned in a direction substantially perpendicular to the main scanning direction, thereby forming the scanning area. In this modification, overlap areas 158 are provided between the scanning areas 155. To acquire low coherent tomographic data, data on the scanning areas are recorded in a recording unit (not shown), and volume data is generated from the recorded data by an image forming unit.

Third Embodiment

Correction of Image Misalignment Due to Involuntary Eye Movement

Observation of the human eyeground in the first and second embodiments of the present invention will be considered. There is a human phenomenon called involuntary eye movement. Therefore, even during observation of the eyeground, the eyeground moves relative to the optical system.

For example, a countermeasure against the movement will be described with reference to FIGS. 4A and 4B for the first embodiment. The relationship among the signal acquisition positions in the scanning areas 145a, 145b, and 145c at a certain instant does not change. Upper left portions of the scanning areas in the figures are acquired simultaneously.

When a movement, such as involuntary eye movement, does not occur, an image on a lower side of the scanning area 145c and an image on an upper side of the scanning are 145b are supposed to nearly coincide with each other. However, when involuntary eye movement occurs, the image on the lower side of the scanning area 145c and the image on the upper side of the scanning area 145b do not coincide.

Figure 9B:
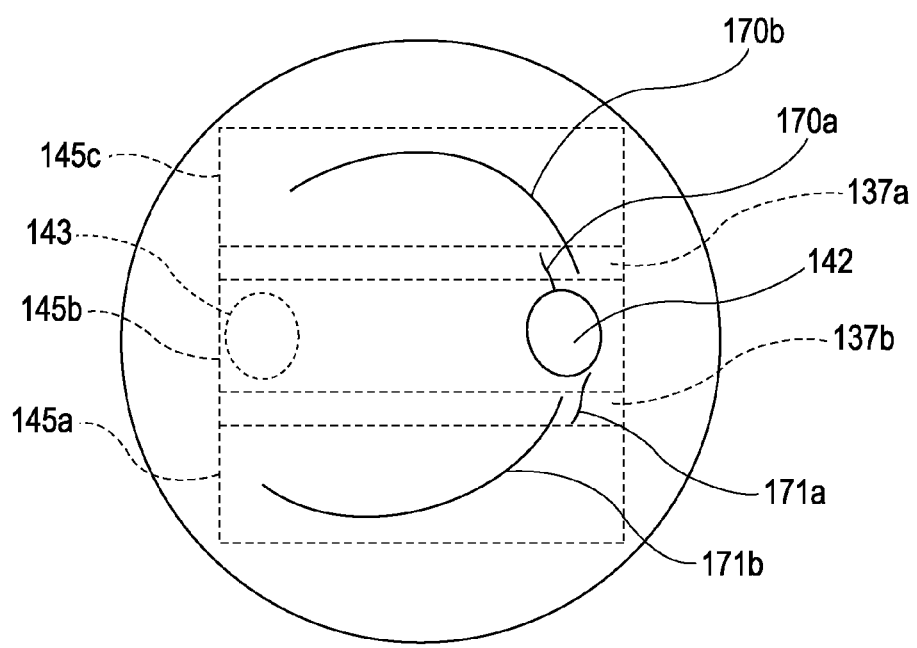
FIG. 9B is an explanatory view showing a third embodiment.

This case will now be described with reference to FIG. 9B. FIG. 9B schematically shows image misalignment caused when involuntary eye movement occurs in an apparatus similar to the apparatus of the first embodiment.

Scanning areas 145a, 145b, and 145c are obtained by scanning beams. Lines 170a and 170b are identical and lines 171a and 171b are identical on the eyeground, but are misaligned by, for example, involuntary eye movement. It is known from the configuration of the apparatus that images in two scanning areas should nearly coincide in overlap areas 137a and 137b.

Hence, it can be determined, on the basis of the amount of image misalignment in the overlap area, whether or not the movement has occurred. FIG. 11 is a flowchart showing an image forming procedure in the third embodiment. This procedure is performed in a control circuit 134.

First, in STEP 1, measurement of a tomographic image of the eyeground starts. Next, in STEP 2, an eye to be examined is aligned with the apparatus. When alignment is properly performed, tomographic measurement starts in STEP 3. In STEP 4, a tomographic image of each area of the eyeground is taken. In STEP 5, signal acquisition is finished. If signal acquisition is not properly performed, measurement is performed again in STEP 4. In STEP 6, analysis of an image of a predetermined overlap area is started. In STEP 7, it is determined whether or not there is a movement in the analyzed overlap area. If there is a movement, the moving amounts in first and second areas are calculated in STEP 8. In STEP 9, a third image is selected in accordance with the moving amounts. When there is no movement in the overlap area in STEP 7, the procedure proceeds to STEP 10. In STEP 10, image synthesis is performed according to the previous operations. In STEP 11, a final tomographic image is output.

In the third embodiment, the third image is formed or the first or second image is used in place, in accordance with the amount of image misalignment in the overlap area. However, in a case in which there is no movement, similar advantages can be obtained even when one of the first image and the second image is selected.

The case of lateral image misalignment has been described above. In some cases, the eye moves in the depth direction (front-rear direction). In such a case of movement in the depth direction, the position relative to the coherence gate changes.

Figure 12A:
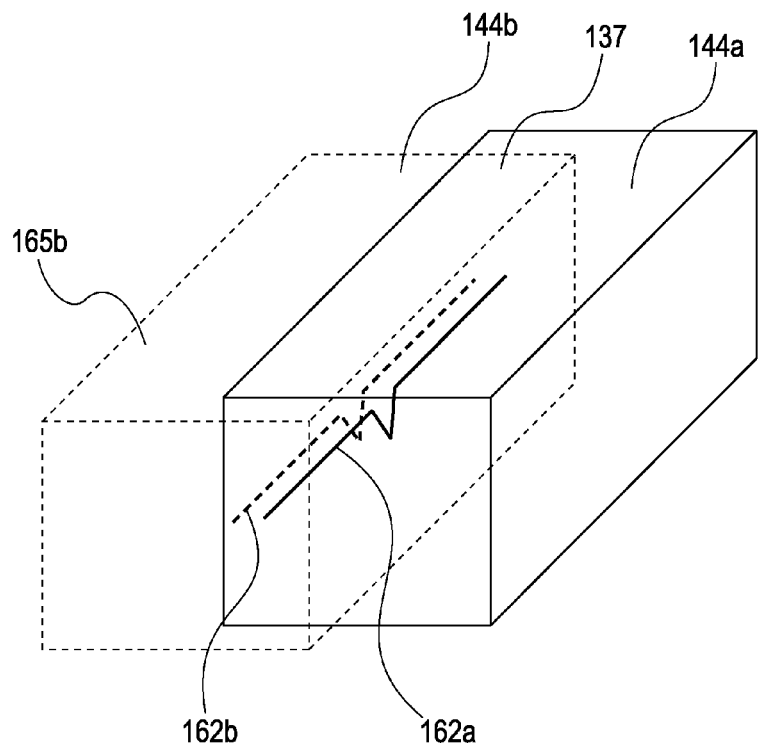
FIG. 12A is an explanatory view showing movement in the depth direction in the third embodiment.
Figure 12B:
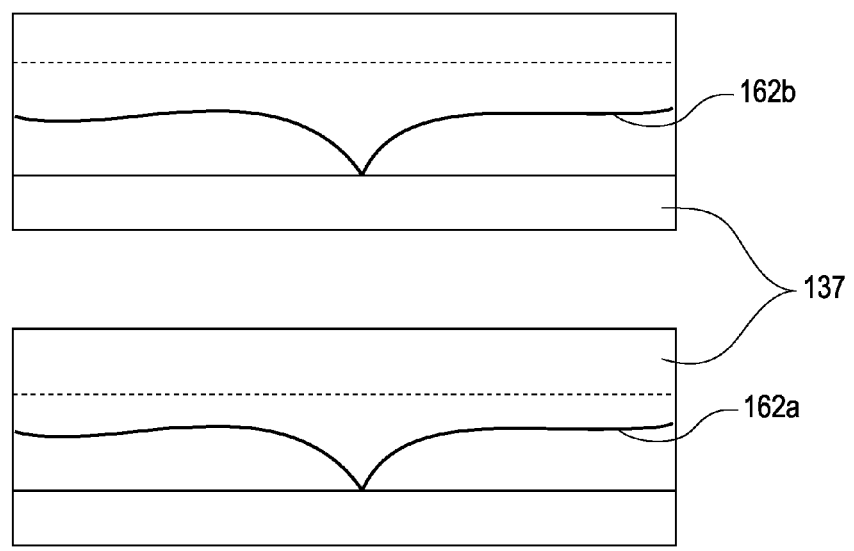
FIG. 12B is an explanatory view showing the movement in the depth direction in the third embodiment.

FIG. 12A shows a case in which a movement occurs in the front-rear direction while scanning areas 144b and 144a are obtained. In FIG. 12A, the movement in the front-rear direction occurs at a start point and an end point in each scanning area. An upper part of FIG. 12B shows a tomographic image at the start point in the scanning area 144a, and a lower part of FIG. 12B shows a tomographic image at the end point in the scanning area 144a. Both images are acquired in the overlap area 137 and correspond to almost the same position, although the images are taken at different times. For this reason, the images nearly coincide unless there is a movement in the depth direction.

Since the scanning loci of the spots are different, as in the first embodiment, the third image is normally generated by the control unit on the basis of these two images.

However, since the images are obtained at different times, it is sometimes better to display only one image when a movement occurs.

In view of these circumstances, while a third image can be generated as an image of the overlap area on the basis of both the first and second images, for example, when a large movement occurs, one of the first and second images whose moving amount is smaller may be used as the third image.

In such a case of displacement in the depth direction, image formation can be realized by performing a procedure similar to that in the flowchart of FIG. 11 in a control circuit.

Fourth Embodiment

SS-OCT

Figure 10:
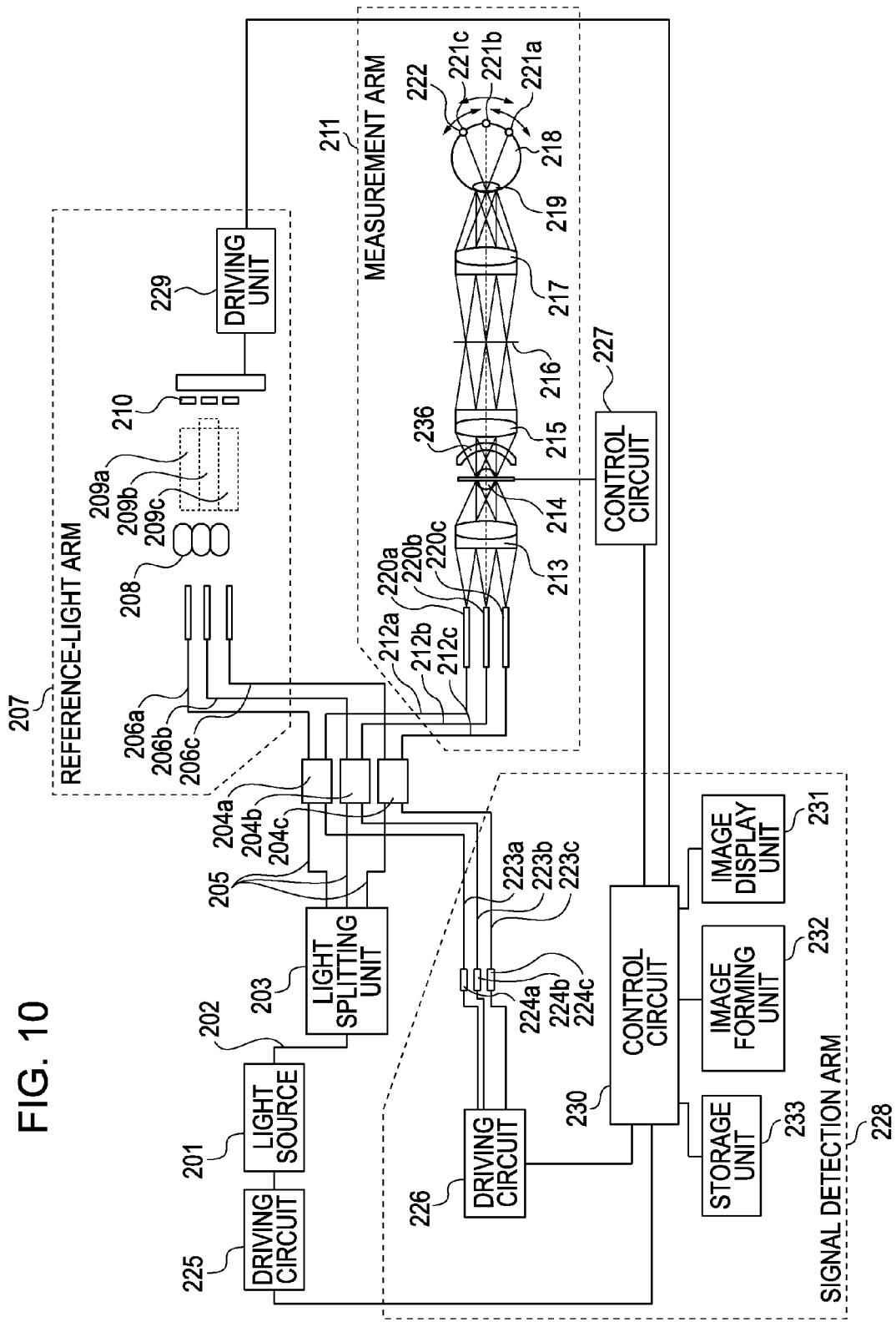
FIG. 10 is a schematic structural view showing a fourth embodiment.

A fourth embodiment will be described below. FIG. 10 schematically shows a configuration of the fourth embodiment. While the first embodiment adopts spectral domain OCT (SD-OCT) in Fourier domain OCT, the fourth embodiment adopts swept source OCT (SS-OCT) in Fourier domain OCT.

A light source 201 is a wavelength variable light source that can sweep near-infrared light at high speed. Light emitted from the light source 201 propagates through an optical fiber 202, and is split toward three optical fibers 205 by a light splitting unit 203. The split light beams in the optical fibers 205 are split by optical couplers 204 (204a, 204b, and 204c) toward a reference-light arm 207 and a measurement arm 211.

The reference-light arm 207 will be described below. Near-infrared light beams exiting from optical fibers 206a, 206b, and 206c enter an optical block 209 (a glass block or a dispersion compensator) via collimating optical systems 208, are reflected by reflective mirrors 210, retrace the optical paths, and enter the optical fibers 206a, 206b, and 206c again. The optical block 209 is composed of optical block elements 209a, 209b, and 209c corresponding to the optical paths, and compensates for dispersion of the optical system in the reference-light arm 207. The reflective mirrors 210 are connected to a reflecting-position control unit 231 so as to independently control the optical path lengths, and is controlled by a driving unit 229 for driving the reflecting-position control unit 231.

The measurement arm 211 will now be described. The light beams split by the optical couplers 204 respectively exit from fiber ends 220a, 220b, and 220c via optical fibers 212a, 212b, and 212c. The light beams exiting from the fiber ends 220a, 220b, and 220c are made substantially parallel by an optical system 213, and the principal rays of the light sources exiting from the exit ends 220a, 220b, and 220c intersect at a deflection point of a scanning unit 214.

The scanning unit 214 is formed by a galvanometer mirror having a rotatable mirror surface, and deflects incident light. The scanning unit 214 is connected to a driving circuit 227 for driving the scanning unit 214. Here, the scanning unit 214 is a two-dimensional scanning unit including two galvanometer mirrors, and is capable of scanning in two directions, that is a main scanning direction in the plane of the figure and a sub-scanning direction perpendicular to the plane of the figure. The light beams scanned by the scanning unit 214 are caused by an imaging lens 215 to form conjugate images of the fiber ends 220 on an intermediate imaging plane 216. The images on the intermediate imaging plane 216 pass through an objective lens 217 and a pupil 219, and form, on a retina 222 of an eye 218 to be examined, irradiation spots 221a, 221b, and 221c corresponding to the fiber ends 220a, 220b, and 220c.

When subjected to in-plane deflection by the scanning unit 214 (direction 236), the irradiation spots 221a, 221b, and 221c move on the retina 222, as shown by the arrows. Reflected light beams from the irradiation spot positions retrace the optical paths, enter the fiber ends, and return to the optical couplers 204a, 204b, and 204c.

A signal detection arm 228 detects interference of the light beams returning from the reference-light arm 207 and the measurement arm 211.

In the signal detection arm 228, the light beams propagating through optical fibers 223a, 223b, and 223c enter photodetectors 224 (224a, 224b, and 224c), respectively.

The light source 201 is connected to a driving circuit 225 for driving the light source 201, and the wavelength of light emitted therefrom is swept at high speed. In synchronization with sweeping, the photodetectors 224 acquire data at high speed, and signals of the data are recorded in a recording unit 233 by a driving circuit 226 for driving the photodetectors. Further, the scanning unit 214 is connected to the driving circuit 227 for driving the scanning unit 214. The driving circuits 225, 226, and 227 are synchronized by a control circuit 230. By analyzing signals output from the photodetectors by wavelength sweeping, tomographic images of the eyeground are taken.

Similarly to the first embodiment, overlap areas 234 are set between the scanning areas of the spots. Volume data is generated by an image forming unit 232 on the basis of data on the scanning areas.

The layout of the scanning areas on the retina may be similar to those adopted in the first and second embodiments.

By thus simultaneously scanning a plurality of light spots over a predetermined area, data can be acquired at a speed increased corresponding to the number of spots.

Further, similarly to the first embodiment, assuming that the spot size on the eyeground is designated as "spot" in consideration of spreading of the spot on the surface of the retina, noise due to crosstalk can be reduced by setting the distance Wd between the irradiation spots as follows:

$$Wd > 2*\text{spot} \tag{1}$$

While light from one light source of a wavelength sweeping type is split by the light splitting unit in the fourth embodiment, similar advantages can also be obtained by using three different light sources of a wavelength sweeping type.

While the scanning unit is formed by a galvanometer mirror in the first and third embodiments, for example, similar advantages can also be obtained even when two galvanometer minors of a one-dimensional deflection type are combined or the scanning unit is a mirror of a two-dimensional deflection type. For higher speed scanning, a resonance scanning mirror, a polygonal mirror, or a solid-state scanning unit, such as an optical crystal, may be provided.

In the case in which involuntary eye movement and the movement in the depth direction occurs, as in the third embodiment, a more accurate image can be formed by changing the method for generating the third image in accordance with the amount of movement.

Other Embodiments

Aspects of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-333869, filed Dec. 26, 2008, which is hereby incorporated by reference herein in its entirety.

The invention claimed is:

1. An imaging apparatus for acquiring plurality of tomographic images of a subject's eye based on a plurality of combined lights formed by combining a plurality of return lights from the subject's eye irradiated with a plurality of measurement lights and a plurality of reference lights corresponding to the plurality of measurement lights, the imaging apparatus comprising:
- a scanning unit configured to scan the plurality of measurement lights on scanning areas of an eyeground of the subject's eye, a part of adjacent scanning areas being overlapped with each other; and
- an acquisition unit configured to acquire an image of the eyeground based on tomographic image information about the eyeground in the scanning areas.

2. The imaging apparatus according to claim 1, further comprising:
- first and second interference units having reference-light paths and measurement-light paths; and
- an optical unit configured to concentrate lights from the measurement-light paths of the first and second interference units at first and second irradiation positions on an eyeground;
- wherein the acquisition unit is configured to acquire first tomographic information and second tomographic information in the first and second scanning areas from interference lights in the first and second interference units, and
- wherein third tomographic information is acquired from the first tomographic information and the second tomographic information in the first and second scanning areas on the basis of the first tomographic information and the second tomographic information in the overlap area.

3. The imaging apparatus according to claim 2, wherein a distance on the eyeground between spots of the lights concentrated at the first and second irradiation positions is more than or equal to the sum of diameters of the spots.

4. The imaging apparatus according to claim 2, wherein the lights from the optical unit are concentrated at the first and second positions on the eyeground by being caused to intersect in an anterior eye segment.

5. The imaging apparatus according to claim 2, further comprising:
- a splitting unit configured to split light into light to be guided to the first interference unit and light to be guided to the second interference unit; and an image forming unit configured to form a tomographic image from the third tomographic information,
- wherein interference lights in the first and second interference units are obtained by interference between return light from the eyeground and return light from the reference-light paths,
- wherein the control unit controls the scanning unit so as to form a correlation between positions of the first and second scanning areas, and
- wherein the third tomographic information is any of the first tomographic information, the second tomographic information, and information obtained by synthesizing the first tomographic information and the second tomographic information in the overlap area.

6. The imaging apparatus according to claim 2,
wherein the optical unit includes a lens, and
wherein first and second dispersion compensating units are provided in the reference-light paths of the first and second interference units so as to compensate for dispersion caused by transmission of the lights from the measurement-light paths from the first and second interference units through the lens.

7. The imaging apparatus according to claim 1,
wherein the scanning areas overlap in a sub-scanning direction of the scanning, and wherein pieces of tomographic information that are adjacent in a main scanning direction of the scanning are aligned on the basis of tomographic information in the overlap area, of a plurality of pieces of tomographic information acquired in a plurality of scanning areas.

8. The imaging apparatus according to claim 1, wherein the acquisition unit acquires the image based on a position gap of the tomographic image information of the eyeground in the overlapped areas.

9. The imaging apparatus according to claim 1, wherein the acquisition unit acquires the image by combining the tomographic images of the eyeground in the scanning areas using the tomographic images in the overlapped areas.

10. The imaging apparatus according to claim 1, wherein the acquisition unit acquires the image by aligning the tomographic images of the eyeground in the scanning areas using the tomographic images of the eyeground in the overlapped areas.

11. The imaging apparatus according to claim 1, wherein the acquisition unit comprises a calculation unit for calculating amount of a position gap of the tomographic image information of the eyeground in the overlapped areas and acquires the image based on a calculation result of the calculation unit.

12. An imaging apparatus for acquiring at least an image of an eyeground of a subject's eye by optical coherence tomography, the imaging apparatus comprising:
- an optical unit configured to concentrate measurement lights at different irradiation positions on the eyeground in a direction intersecting an axis of an optical path common to the measurement lights; and
- a tomographic-information acquisition unit configured to acquire tomographic information about the eyeground using the measurement lights,
- wherein the optical unit is configured to simultaneously make the measurement lights incident on an anterior eye segment of the subject's eye so that the measurement lights intersect each other at the anterior eye segment.

13. An imaging method for acquiring a plurality of tomographic images of a subject's eye based on a plurality of combined lights formed by combining a plurality of return lights from the subject's eye irradiated with a plurality of measurement lights and a plurality of reference lights corresponding to the plurality of measurement lights, the imaging method comprising:
- scanning the plurality of measurement lights on scanning areas of an eyeground of the subject's eye, a part of adjacent scanning areas being overlapped with each other; and
- acquiring an image of the eyeground based on tomographic information about the eyeground in the scanning areas.

14. The imaging method according to claim 13,
wherein the scanning areas overlap in a sub-scanning direction of the scanning, wherein pieces of image information that are adjacent in a main scanning direction of the scanning are aligned on the basis of tomographic information in the overlap area, of a plurality of pieces of tomographic information acquired in the plurality of scanning areas.

15. A computer-readable storage medium configured to store a program that causes a computer to perform the imaging method according to claim 13.

16. An imaging apparatus for acquiring at least an image of an eyeground of a subject's eye by optical coherence tomography, the imaging apparatus comprising:
- an optical unit configured to make measurement lights incident on an anterior eye segment of the subject's eye and to concentrate the measurement lights at different irradiation positions on the eyeground in a direction intersecting an axis of a common optical path of the measurement lights; and a tomographic-information acquisition unit configured to acquire tomographic information about the eyeground using the measurement lights, wherein the optical unit includes a common scanning unit configured to scan the concentrated measurement lights on the eyeground and arranged on the common optical path.

17. The imaging apparatus according to claim 16, further comprising:

a common dispersing unit configured to disperse combined lights of return lights from the subject's eye combined with reference lights corresponding to the measurement lights and arranged on a common optical path of the combined lights, wherein the tomographic-information acquisition unit is configured to acquire tomographic information about the eyeground using the dispersed combined lights.

18. The imaging apparatus according to claim 17, further comprising:

a plurality of detection units configured to detect each of the dispersed combined lights.

19. The imaging apparatus according to claim 17, further comprising:

a moving unit configured to change an optical path length of the reference lights and arranged on a common optical path of the plurality of reference lights.

20. The imaging apparatus according to claim 16, wherein the optical unit is configured to simultaneously make the measurement lights incident on the anterior eye segment of the subject's eye so that the measurement lights intersect each other at the anterior eye segment.

21. The imaging apparatus according to claim 16, wherein the common scanning unit is single.

22. An imaging apparatus for acquiring at least an image of an eyeground of a subject's eye by optical coherence tomography, the imaging apparatus comprising:

an optical unit configured to make measurement lights incident on an anterior eye segment of the subject's eye and to concentrate the measurement lights at different irradiation positions on the eyeground in a direction intersecting an axis of an optical path common to the measurement lights;

a common dispersing unit configured to disperse combined lights of return lights from the subject's eye combined with reference lights corresponding to the measurement lights and arranged on a common optical path of the combined lights; and a tomographic-information acquisition unit configured to acquire tomographic information about the eyeground using the dispersed combined lights.

23. The imaging apparatus according to claim 22, further comprising:

a plurality of detection units configured to detect each of the dispersed combined lights.

24. The imaging apparatus according to claim 22, further comprising:

a moving unit configured to change an optical path length of the reference lights and arranged on a common optical path of the plurality of reference lights.

25. The imaging apparatus according to claim 22, wherein the optical unit is configured to simultaneously make the measurement lights incident on the anterior eye segment of the subject's eye so that the measurement lights intersect each other at the anterior eye segment.

26. The imaging apparatus according to claim 22, wherein the common dispersing unit is single.

27. An imaging apparatus for acquiring at least an image of an eyeground of a subject's eye by optical coherence tomography, the imaging apparatus comprising:

an optical unit configured to make measurement lights incident on an anterior eye segment of the subject's eye and to concentrate the measurement lights at different irradiation positions on the eyeground in a direction intersecting an axis of an optical path common to the measurement lights;

a common moving unit configured to change an optical path length of a reference lights corresponding to the measurement lights and arranged on a common optical path of the reference lights; and a tomographic-information acquisition unit configured to acquire tomographic information about the eyeground using combined lights of return lights from the subject's eye combined with the reference lights.

28. The imaging apparatus according to claim 27, wherein the optical unit is configured to simultaneously make the measurement lights incident on the anterior eye segment of the subject's eye so that the measurement lights intersect each other at the anterior eye segment.

29. The imaging apparatus according to claim 27, wherein the common moving unit is single.

30. An imaging apparatus that takes an image of an eyeground by optical coherence tomography, the imaging apparatus comprising:

an optical unit configured to concentrate a plurality of measurement light beams incident on an anterior eye segment at a plurality of irradiation positions on the eyeground, and including a scanning unit configured to scan the concentrated measurement light beams over the eyeground;

a tomographic-information acquisition unit configured to acquire tomographic information about the eyeground using the measurement light beams; and a control unit configured to control the scanning unit so that the measurement light beams concentrated at the irradiation positions are scanned in a plurality of scanning areas of the eyeground and so that adjacent scanning areas, of the plurality of scanning areas, overlap with each other.

31. An imaging method that takes an image of an eyeground by optical coherence tomography, the imaging method comprising:

a light concentration step of concentrating a plurality of measurement light beams incident on an anterior eye segment at a plurality of irradiation positions on the eyeground;

a scanning step of scanning the concentrated measurement light beams in a plurality of scanning areas of the eyeground in a manner such that adjacent scanning areas, of the plurality of scanning areas, overlap with each other; and a tomographic-information acquisition step of acquiring tomographic information about the eyeground using the measurement light beams.

32. A computer-readable storage medium configured to store a program that causes a computer to perform the imaging method according to claim 31.

* * * * *